United States Patent [19]

Lee

[11] Patent Number: 4,679,569
[45] Date of Patent: Jul. 14, 1987

[54] BALLISTOCARDIOGRAPH

[76] Inventor: Arnold St. J. Lee, 2008 Cotner Ave., Los Angeles, Calif. 90025

[21] Appl. No.: 795,894

[22] Filed: Nov. 7, 1985

Related U.S. Application Data

[63] Continuation-in-part of Ser. No. 786,746, Oct. 11, 1985.

[51] Int. Cl.⁴ .............................................. A61B 5/02
[52] U.S. Cl. ................................... 128/714; 128/135; 269/328
[58] Field of Search ............... 128/714, 774, 1 R, 670, 128/134, 135; 5/81 R; 269/328

[56] References Cited

U.S. PATENT DOCUMENTS 1,078,090  11/1913  Foss ...................................... 5/81 R
2,751,268  12/1953  Credman ............................ 269/328

OTHER PUBLICATIONS

"Ballistocardiography with Elimination of the Influence of Vibration Properties of the Body", W. von Wittern, *American Heart Journal*, vol. 46, Nov. 1953, pp. 705–714.

*Primary Examiner*—Kyle L. Howell
*Assistant Examiner*—Randy Citrin
*Attorney, Agent, or Firm*—Spensley Horn Jubas & Lubitz

[57] ABSTRACT

Disclosed is an improved ballistocardiograph system, apparatus and method. Basic to the system of the present invention is a first rigid individualized mold having preferably a negative impression of the dorsal half of the body. The body mold rigidizes the body thereby facilitating the preparation of a ballistocardiogram. Additional rigidizing is provided by a second rigid mold, connected to the first mold, having preferably an exact negative impression of the ventral half of the body. The system can also include means for substantially eliminating artifacts created by movements of the body mold not caused by the subject.

25 Claims, 11 Drawing Figures

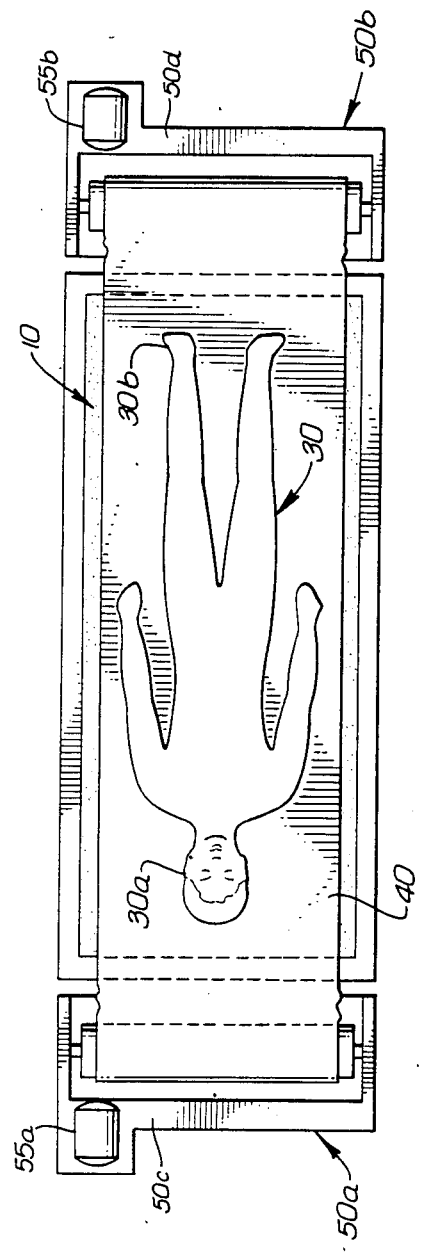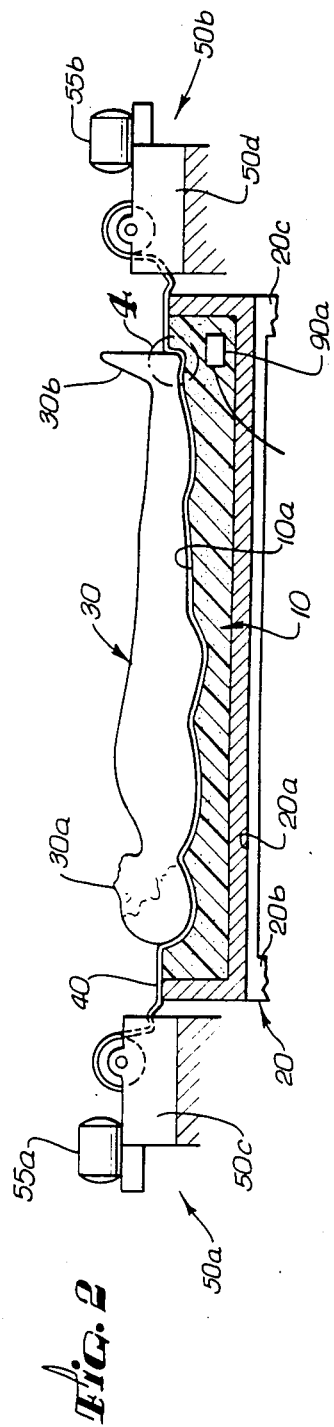
Fig. 1
Fig. 2

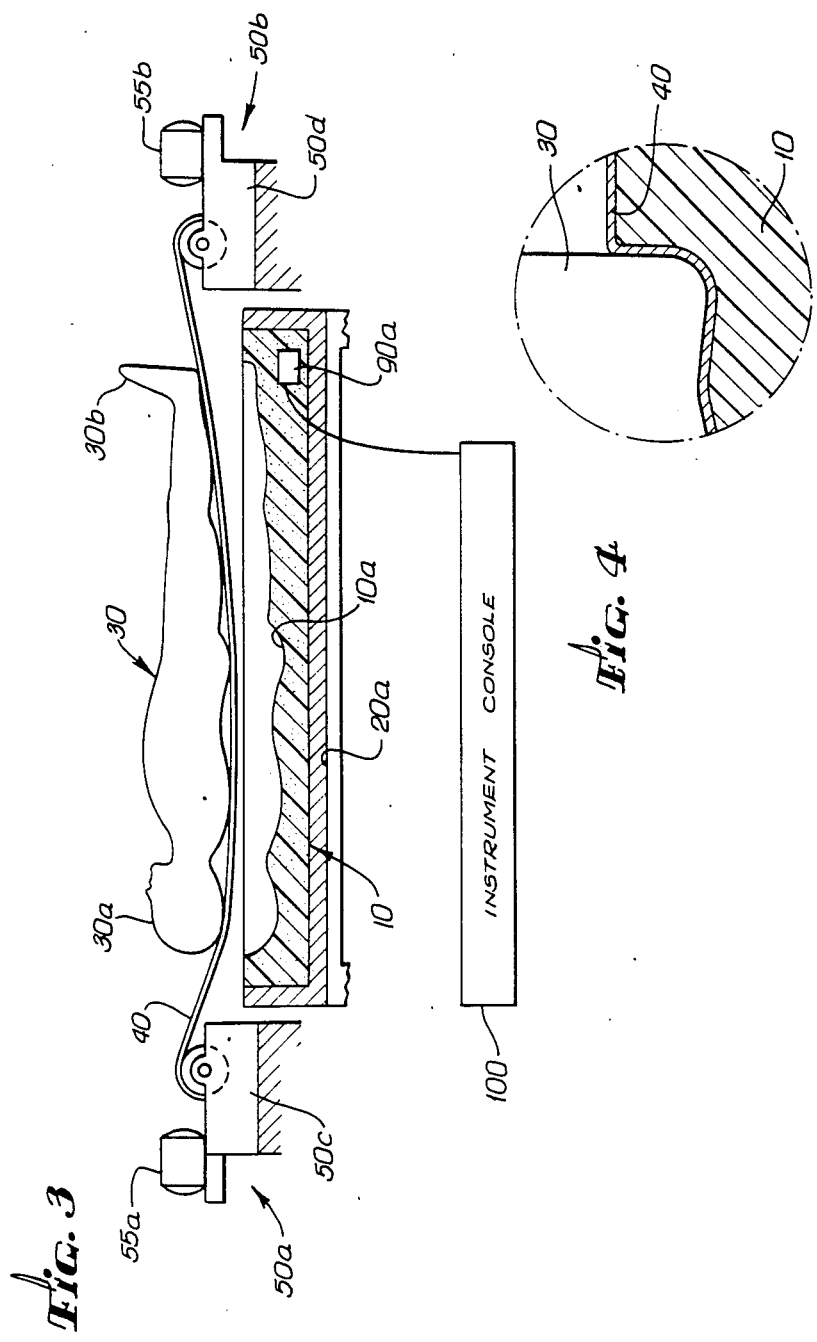

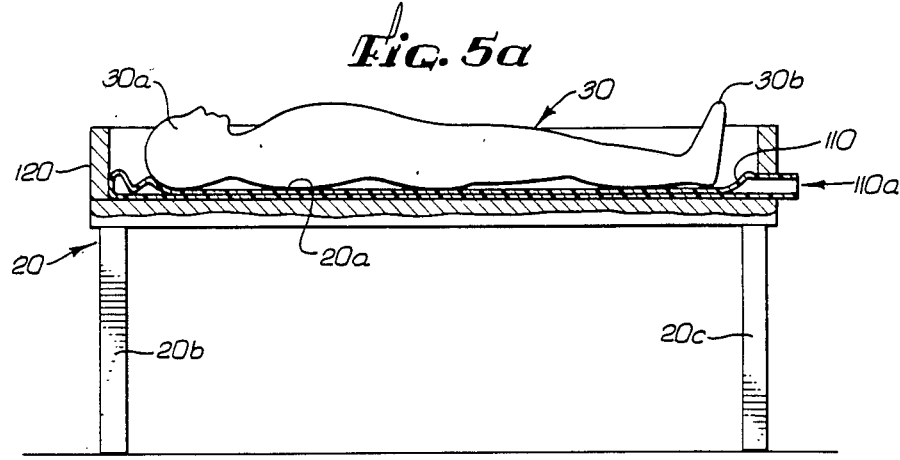
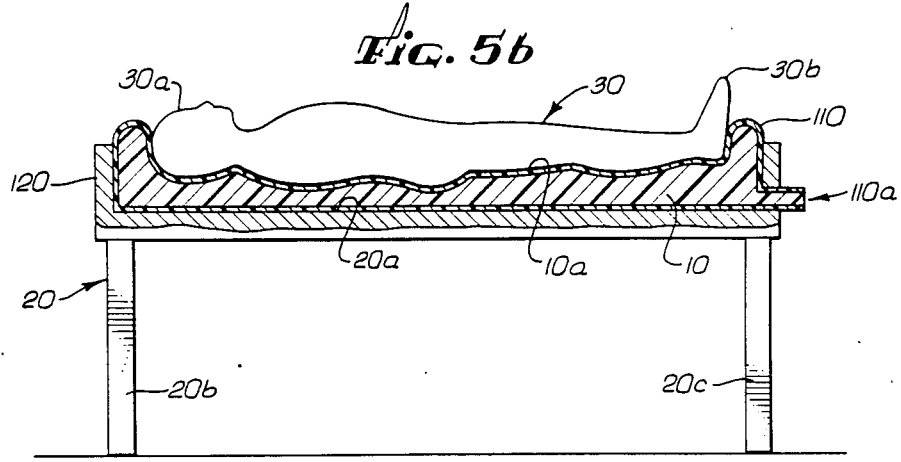
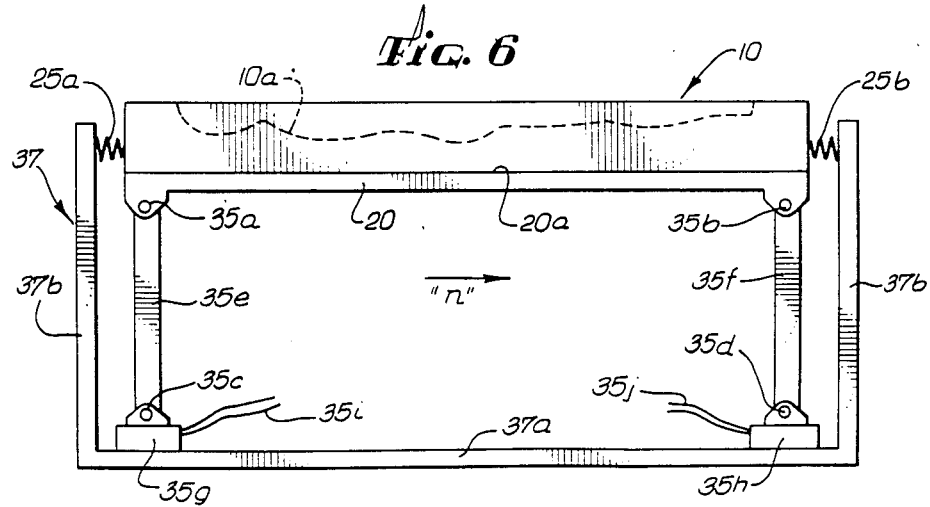

BALLISTOCARDIOGRAPH

RELATED APPLICATIONS

This is a continuation-in-part of application Ser. No. 786,746, filed Oct. 11, 1985, and owned by the inventor, Arnold St. J. Lee.

FIELD OF THE INVENTION

The present invention relates to the field of medical instrumentation and methods of using such instrumentation in an accurate and reproducible manner. In particular the present invention concerns use of a body mold of a subject to facilitate use of motion sensors to gather physiological data for preparing a ballistocardiograph and the use of a reference mass to eliminate artifacts caused by building movement.

PRIOR ART

To estimate blood flow through the heart there are basically two alternatives. In one alternative, a sensor intrusively enters the body through a vein and through the heart, thereby being a time-consuming, costly and dangerous testing procedure usually reserved for grave situations. The alternative method of ballistocardiography involves placing the subject on a special bed and involves using a motion transducer to measure body movement caused by the heart beat. Ballistocardiography is completely non-invasive, painless, uses no "disposable" or other "expensive-per-use" elements, is quickly accomplished and, if comparative values exist, is easily analyzed.

The ballistocardiograph has been limited in clinical usefulness by the wide variation in the relationship between the actual heart output and a ballistocardiograph wave among the general population. This variation derives from two major sources namely, the anatomic differences among subjects, and "instrumentation" variability caused by the unstable, oscillatory coupling between the source of the ballistocardiograph (the heart and major arteries) and a ballistocardiograph motion transducer or sensor.

Accurate use of a motion transducer requires that the body remain still and free from the effects of external movements such as microseisms in the ground, structural building vibrations, tissue vibrations and tissue elastic coupling. A motion transducer connected to a bed often yields data confused by spurious oscillating connections between the patient and the sensor. Typically, the heart is coupled unstably and oscillatorily to the great arteries, which are themselves resilient and compliant, and both are coupled to the subject's body wall with similar indirectness. The subject's body is then coupled to the ballistocardiograph "bed" or "table" with similar problems caused by the non-rigid (jelly-like) connection of the subject's skin and sub-dermal tissue to the bed. The resonance of the bed/subject conglomerate in its connection to the solid earth provides additional artifacts or noise to the ballistocardiograph recording. The subject's body itself contains mass elements, themselves jelly-like, which contribute other-than-coupling resonances.

The prior art suggests that footboards, and lateral clamps or straps, greatly improve the coupling between the body and bed, and that the dorsal spring constant can be increased by having a rough surface on the bed so that when the subject lies on the bed with the subject's feet against a footboard and knees flexed, full extension of the legs keeps a high tension in the dorsal tissue all during data taking. However, even the better methods of ballistocardiography have not produced the reproducibility and accuracy desired. Moreover, the positioning of the patient with respect to the sensor, electrodes and ballistocardiograph bed, or the positioning of the sensors, electrodes, etc., with respect to the patient has required the services of an attendant skilled in the techniques required.

DESCRIPTION OF THE DRAWINGS

FIG. 1 is a prospective top view of a system of the present invention.

FIG. 2 is a side view of a system of the present invention with the subject's body lying in the body mold depression of the present invention.

FIG. 3 is the same view as FIG. 2 with the subject's body raised out of the body mold depression of the present invention.

FIG. 4 is an enlarged view of a portion of FIG. 2 showing a body/hammock/body mold sandwich.

FIGS. 5a,b shows the body mold bag of the present invention.

FIG. 6 shows a cross-sectional diagram of the body mold of the present invention supported by vertical legs.

SUMMARY OF THE INVENTION

Figure 7:
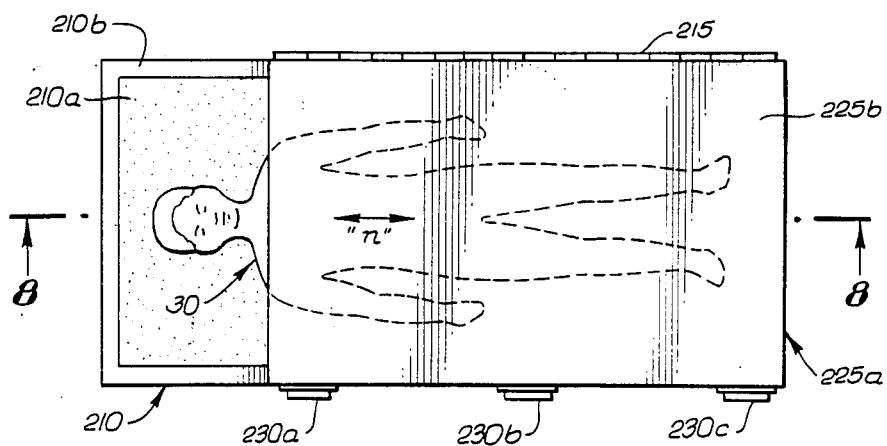
FIG. 7 shows a top view of a ballistocardiograph body mold of the present invention.

In its broadest sense, the present invention comprises a physiological information gathering system. The system can be particularly adapted to provide a method of in-home, self monitorization for elderly, sickly and health-concerned persons without the assistance or required presence of an attendant.

Basic to the system of the present invention is an individually made rigid body mold having a negative impression of a portion of the lower half of the body when the body is in a supine position (a depression intimately matching the dorsal half of the body). The body portion is confined by the body mold and is held inside it by gravity. In addition to insulating the body from the effects of external movements, the body mold also accurately and reproducibly positions the body and keeps the body stationary. By embedding or connecting sensors to the body mold at specific locations, the sensors will also be accurately and reproducibly positioned next to a specific body location each time the subject lies in the body mold. As a result, the data gathered by the sensors will provide accurate and reproducible measurements of physiological conditions. Means also are provided for conveniently moving a subject's body into and out of the body mold depression. The system overall provides significant advances in ballistocardiography.

One particular aspect of the present invention addresses the unstable, oscillatory, non-reducible coupling between the subject and a ballistocardiograph bed, and the additional resonances caused by local "islands" of somewhat independently-suspended (jelly-like) mass elements comprising the subject's body. This invention, using a new kind of "bed", constrains both the subject's body and its relationship to the ballistocardiograph bed thereby rigidizing previously unstable and oscillatory elements. This aspect of the present invention consists of a bed and a method of recording a ballistocardiograph record using that bed.

The bed of the present invention consists of an individually-shaped body mold of rigid, low-density material, an upper portion having a depression intimately matching at least a portion of the ventral half of the body except for the head, it being hinged to the lower body mold portion as discussed above, i.e., a mold, having a depression intimately matching at least a portion of the dorsal half of the body. Preferably, the subject lies in a hinged mold of the entire body except for the ventral of the head, which otherwise exactly fits the natural contours of the subject's body. This close fitting rigidizes the body and insures that each time the subject returns to the ballistocardiograph apparatus, his body achieves the identical relationship to the apparatus. Further, the coupling between the subject's body and the mold occurs intimately over a very large area, while the volumetric restraint caused by the non-distensible body mold cavity greatly reduces self-oscillatory and coupling resonances. The body mold, suitably braced, functions as the ballistocardiograph "bed" and is otherwise used with motion transducers, motion limiting supports and motion modifying elements.

DETAILED DESCRIPTION OF THE DRAWINGS

The following description is the best presently contemplated mode of carrying out the invention. This description is made for the purpose of illustrating the general principles of the invention and is not to be taken in a limiting sense. The scope of the invention is best determined by reference to the appended claims.

In general, the present invention comprises a system, apparatus and method for gathering physiological data to provide useful physiological information to the health conscious. In one embodiment of the invention, and with reference to FIGS. 1-4, the system of the present invention includes body mold 10 resting on table 20 having flat, planer upper surface 20a and preferably with four vertical table supports 20b,c (two are not shown) extending from each corner of the table. The dorsal half of a body 30 is shown lying in a negative impression 10a of the body mold 10. Sandwiched between the body 30 and the depression surface is resilient hammock 40. Extending from the top of the table 20, adjacent the head 30a and feet 30b of the body 30, are motorized hammock roller mechanisms 50a,b. The hammock 40 and the roller mechanisms 50a,b function to lift the body 30 out of, and place the body into, body mold depression 10a by making the hammock 40 rigid and flaccid, respectively. The accelerometer 90a, which is embedded in the body mold 10, is connected to instruments contained in console 100.

The body mold 10 can be made of any firm, structurally rigid material, such as polyurethane isocyanate foaming plastic system. The body mold 10 is preferably made of a low density, high modulus, foaming plastic such as that sold under the trademark "Structural Rigid Foam" by Polymer Development Laboratories, Inc. The foaming plastic is preferred due to its lightness, its low thermal conductivity and stiffness.

The body mold 10 can be individually prepared in a variety of ways; however, one way is preferred. With reference to FIGS. 5a,b, a thin plastic or rubber bag 110 having an opening 110a is placed within a mold form 120 (which is removed after mold is made) on a flat surface such as that of the upper surface 20a of the table 20. Bag opening 110a is adapted to receive nozzle (not shown) of mixing injection pump machine (not shown). Body 30 lies in a supine position on uninflated bag 110. The bag 110 is then injected with a foaming plastic mixture thereby simultaneously raising the patient off of the flat table and creating a depression 10a. By filling the bag about one-half the way up the body width, and allowing the foaming plastic or rubber to solidify, removal of the bag followed by trimming of the rough body mold will reveal the finished body mold 10. Generally, the low density foam is quick-setting. Some foaming plastics form an integral skin which results in the body mold having a tough, outer skin. Alternatively, the addition of an epoxy coat to the body mold strengthens the body mold surface.

Another way of preparing the body mold 10 involves cutting the dorsal impression from a solid plastic foam block. Optical sensor systems are available to generate a graphical representation of the subject's body which can be used to properly cut out the dorsal impression. However, since the graphical representation does not include the effects of gravity on the dorsal tissue, it is not a preferred method.

After the body mold is prepared, body mold 10 is firmly affixed to table or bed 20 which is connected by springs, preferably weak centering springs 25a,b to rigid frame 37 having a base 37a connected to, or resting on, the floor, and rigid arms 37b extending from the base 37a. The bed 20 is connected by low friction axles 35a,b,c,d to rigid vertical support panels 35e,f which are in turn connected to pedestals 35g,h, each having a weight or vertical force transducer (not shown) including a preamplifier. A preferred construction of the vertical support panels is more clearly shown in FIG. 9. It should be appreciated that the axles 35a-d have captured knife-edge connections which help eliminate friction effects. It should be appreciated that two vertical support panels are shown, and that the bed vertical support panels are wide in the perpendicular (horizontal) direction so as to facilitate restraining the bed so that it cannot move sideways. That is, the entire system is designed to allow movement only in the linear direction "n", i.e., along the longitudinal axis of the subject. The signals from the transducer are fed via wires 35i,j to a console for recording on an oscillographic recorder.

In the art of ballistocardiography, the slight movement of the body is measured as the body reacts to the blood inertia forces caused by the heartbeat. A motion transducer as, for example, an accelerometer, may be used to generate a ballistocardiogram which is basically a time-based chart of body acceleration, velocity or position data. Recordation of such data into chart form enables one to estimate the heart action and heart output of a patient relative to a previously recorded "baseline".

In one method according to the present invention, an accelerometer is embedded in the body mold so that its active axis is along the longitudinal axis of the body. This is done by making a hole in the mold, inserting the accelerometer, and gluing the accelerometer to the mold. The mold will move in response to the heartbeat, and the longitudinal vibrations will be recorded by the accelerometer. By embedding the accelerometer 90a in the body mold 10, a ballistocardiogram sensor is accurately placed with respect to specific body portions; the body mold keeping the body still and substantially free of the effects of its own oscillations vs. the bed, and external movements. As a result, reproducible data can be obtained and accurate comparison with previous data performed.

To obtain a ballistocardiogram, the body mold may rest upon extremely slippery horizontal linear bearings, or rest upon vertical legs (see FIGS. 6 discussed above and 9 discussed below), in each case constraining the body mold so that it can only move in the longitudinal direction "n".

Figure 8:
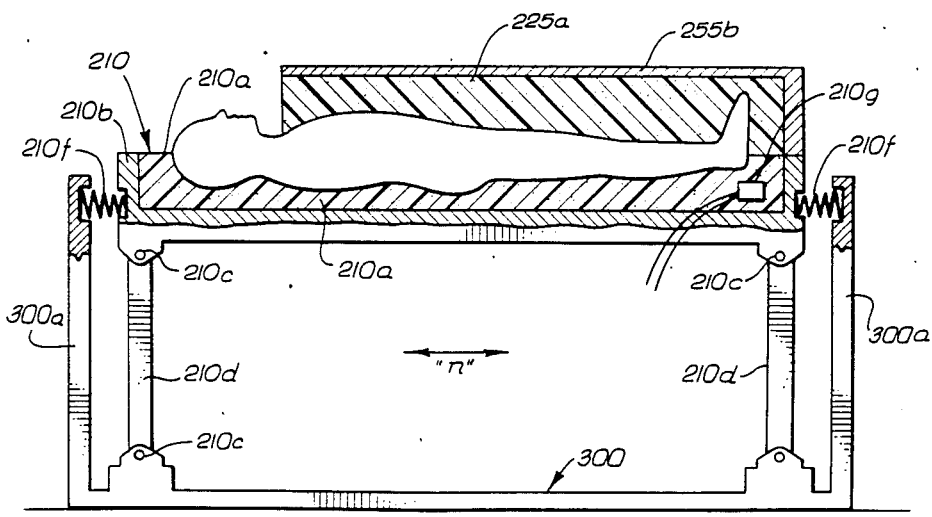
FIG. 8 is a cross-sectional view of the ballistocardiograph body mold of the present invention taken along line 8—8 of FIG. 7.
Figure 9:
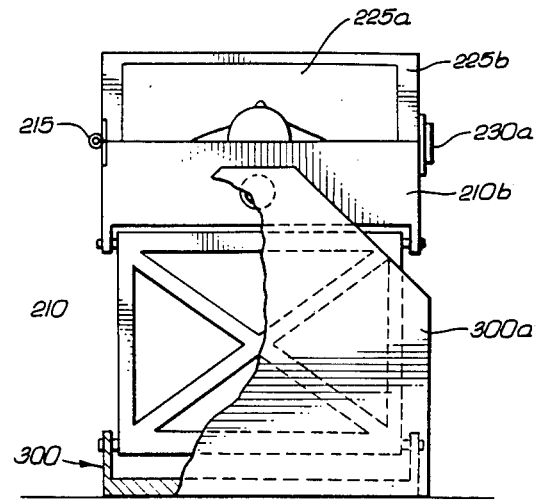
FIG. 9 is a head-on view, partially cut-away, of a ballistocardiograph body mold of the present invention.

With reference also to FIGS. 7, 8 and 9, another embodiment of the ballistocardiograph apparatus of the present invention is shown. The dorsal body mold 210a is surrounded by mold brace or frame 210b. Mold brace 210b is connected by piano hinge 215 to ventral body mold 225a which is held by frame 225b. The ventral body mold 225a, when in a closed position as shown in FIG. 7, is attached to dorsal body mold 210a with bracing hinges and clasps 230a-c. The subject's body in such a closed mold is highly rigidized. As previously noted, the dorsal half body mold rigidizes the body to a great extent, and the ventral half rigidizes the body even more. The degree of rigidizing, of course, depends upon the jelly-like nature of the subject's body.

FIG. 9 shows an end cut-away to show details of the vertical support panels 160 which support the frame 210b and body mold (dorsal and ventral) and act as legs, but constrain the bed to move only in direction "n", i.e., along the longitudinal axis of the subject. The frame 210b is pivotally connected by axles 210c to vertical support panels 210d and base 300 which rests on the floor of a building. The panels 210d preferable comprise cross-supports, and the base 300 includes rigid, plate-like side supports 300a. The ballistocardiograph unit also includes weak centering springs 210f, with one end of the springs 210f connected to frame 210b and the other end of the springs connected to base side support 300a. The axles 210c preferably have knife-edge connections which help eliminate friction effects. An accelerometer or other motion transducer 210g is connected to the dorsal body mold 210a as discussed previously. During operation of the apparatus, the ventral body mold portion 225a is preferably used, and if used, closed over the subject using the hinges and clasps 230a-c, and thereafter a ballistocardiograph is taken.

The ballistocardiograph full body mold of the present invention can be made by the processes discussed above or by other processes known in the art. It should be appreciated that the ventral half of the body mold does not need to cover the face, and that the mold can be of merely a portion of the body rather than the entire body.

It should be appreciated that springs 210f also facilitate restricting the longitudinal movement of the ballistocardiograph unit along the direction "n" shown in the figures. It should also be appreciated that in addition to an accelerometer, other motion transducers can be used in the ballistocardiograph including a displacement or strain guage or a velocity motion transducers. These can be used to produce a ballistocardiograph by suitable differentiation and/or integration.

It should further be appreciated that a ballistocardiograph apparatus is essentially a type of seismograph. Therefore the ballistocardiograph recording may contain noise caused by building movements. As a result, prior art ballistocardiographs were mounted on extremely solid surfaces, such as the ground floor of a building. However, movement of the building still affected the ballistocardiograph.

Figure 10:
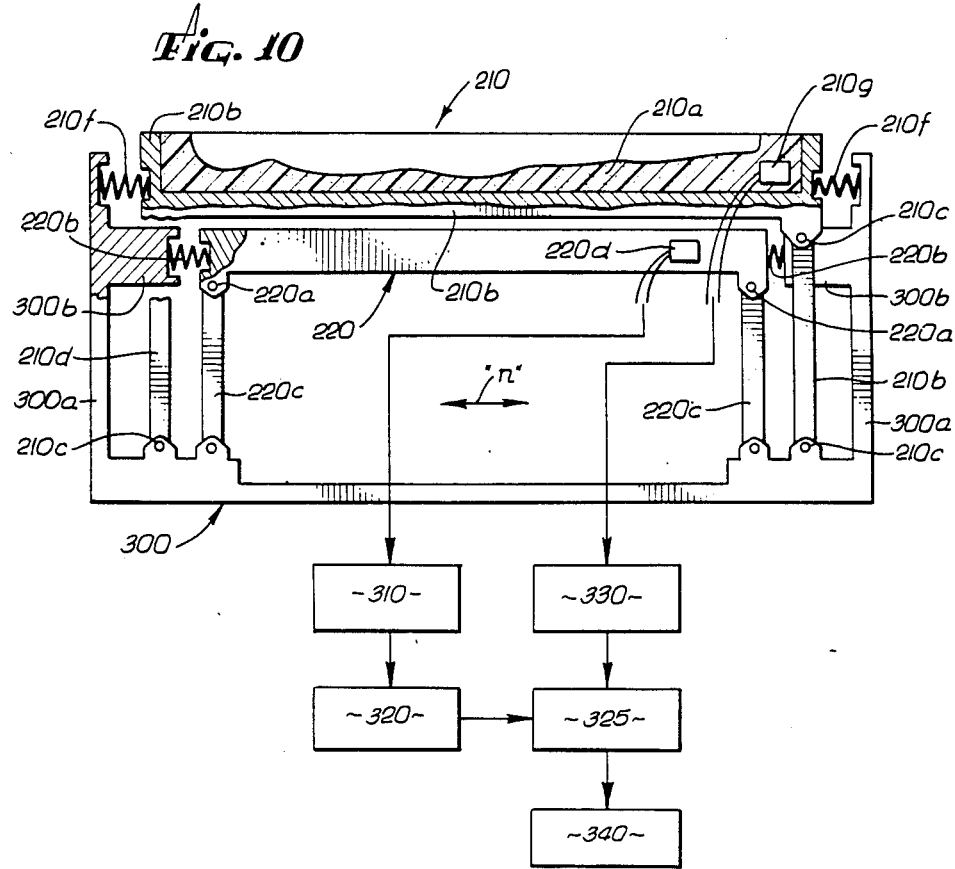
FIG. 10 is a cross-sectional side view, partially cut-away, of the present invention showing a reference unit for ballistocardiograph comparison measurements.

The present invention makes use of the principal of comparison measurement to a reference, as opposed to direct absolute measurement, to cancel the effects of building movements. Therefore, and with reference to FIG. 10, mounted on the same base 300 as the ballistocardiograph unit 210, and contacting the base 300 of the system as close as practical to the ballistocardiograph unit 210, is a generally planar reference unit 220 having a mass $M_{Ref}$. As discussed previously, the ballistocardiograph unit 210 comprises rigid body mold 210a surrounded by rim or frame 210b. Preferably, but optionally, a ventral body mold portion can also be used. The ballistocardiograph frame 210b is pivotally connected by axles 210c to vertical side support panels 210d which are connected by axles 210c to base 300. (It should be appreciated that a portion of the upper left portion of FIG. 10 is cut-away to show the mounting of the reference unit 220 as discussed further below.) The frame 210b is further connected in part to the base vertical support 300a by weak centering springs 210f. This construction is such that the ballistocardiograph unit 210 is constrained to move only in the horizontal direction "n" if a force is applied to the mold 210a in the direction "n".

The reference unit 220 is similarly connected to vertical side support panels 220c and the base 300 by axles 220a. Weak centering springs 220b connect the mass 220 to extensions 300b of base side supports 300a. The ballistocardiograph unit 210 includes accelerometer or other motion transducer 210g, and the reference unit 220 includes accelerometer or motion transducer 220d.

In operation, the reference unit mass $M_{ref}$ and weak centering springs are chosen to produce the same natural frequency as the ballistocardiograph unit 220. That is, the reference mass spring constant and the reference mass are adjusted so that the natural period of oscillation of the reference mass is the same as that of the ballistocardiograph unit 210 with a mass having the weight of the patient in the body mold. For example, the spring 220b can be adjusted by changing the spring constant as is known in the art or the reference mass can be adjusted by adding or substracting weight from the reference unit 220.

Since the subject's physiological vibrations effect only the ballistocardiograph unit 210, and the movements of the ballistocardiograph base 300 caused by building movements affect both the ballistocardiograph unit 220, and the reference unit 220 equally by creating noise in the ballistocardiograph , by substracting the electrical signal output of the amplified reference motion transducer from the ballistocardiograph motion transducer, most of the building movement noise is cancelled. In operation then, the reference motion transducer or preferably accelerometer 220d is connected to a reference accelerometer amplifier 310 which is connected to a device 320 containing a filter compensator (not shown) and a gain control compensator (not shown) which is in turn connected to a subtraction circuit 325 for subtracting the amplitude of the amplified signal produced by the reference motion transducer from the amplitude produced by the ballistocardiograph motion transducer to yield a value. The ballistocardiograph unit motion transducer or accelerometer 210g is connected to a ballistocardiograph amplifier 330 which is also connected to the same subtraction circuit 325. The output of the subtraction circuit 325 is connected to a recorder 340 for observation. The mass of the reference unit and/or the reference mass spring (constant) are adjusted to match the natural frequency of the ballistocardiograph unit 210 with a mass equal to the mass of the subject in the mold 210a. The filter and gain control are then adjusted so that a disturbance, for example, by kicking the base 300 gently in the direction "n", produces a minimum output signal to the recorder 340, ideally 0. that is, adjustments are made to minimize subtraction circuit value. In other words, because it is very difficult to fabricate two systems with exactly identical characteristics, the output of the reference motion transducer amplifier is passed through a variable, controllable filter and attenuator (gain control). These are used to fine tune the system, i.e., to more exactly compensate for any differences in damping, gain or other phase shifting influences. It should be noted that because the oscillatory movements of the ballistocardiograph unit and the reference unit are miniscule there is no discernable pendulum effect of the support legs 210d and 220c.

The system of the present invention is particularly useful to the elderly and invalid. The system can include a transfer mechanism to enable conveniently transferring the body 30 into and out of the body mold 10. The transfer mechanism includes head roller mechanisms 50a, foot roller mechanisms 50b, supports 50c and d, and rollable hammock 40 having one end connected to roller mechanism 50a and the other end connected to roller mechanism 50b. A motor drive 55a,b is provided for the head roller and the foot roller, respectively. The hammock can be made of a cloth sheet or membrane, for example, a nylon knitted fabric which is silky, flexible, thin and relatively non-distensible longitudinally. The hammock contains reinforced holes positioned to allow the electrodes and sensors to contact the skin.

While the body mold is being used, the motors are not activated thereby maintaining the hammock flaccid. The hammock therefore does not significantly effect the contours of the body mold depression. When the motors are forwardly activated, the hammock is tightened. At that point, the subject merely lies down on the hammock. The motors are then operated slowly in reverse to render the hamock flaccid thereby simultaneously placing the body into the depression. After testing is complete, the motors are again forwardly activated to render the hammock taut. The subject can then get off of the hammock. Compare the hammock depicted in FIGS. 2 and 3.

There are a wide variety of variations of the above description which those of skill in the art will recognize as being within the scope of the present invention. For example, the present invention, in one aspect, contemplates a revolution in medical technology. Specifically, the present invention envisions accurate in-home self-monitorization. That is, the body mold "bed" is relatively inexpensive, and can be kept in the home of any person, for example, the elderly and sickly, and used to obtain, as well as transmit, vital sign data to a physician, without the assistance of another person.

I claim:

1. A ballistocardiograph system for accurately and reproducibly preparing a ballistocardiograph of a subject, the system comprising:
steady means for stationing, and thereby reproducibly positioning, a body of the subject by close-fitting confinement and constraint of a large area of skin of the body;
motion limiting means for limiting movement of the steady means to a particular linear direction of movement;
a motion transducer connected to the steady means for producing a ballistocardiograph of body motion caused by blood output through the heart by sensing motion of the steady means within which the body is stationed; and
transfer means for transferring the body into and out of contact with the steady means;
wherein the steady means includes a first rigid body having a negative impression of a portion of the dorsal half of the body of the subject.

2. A system according to claim 1 wherein the transfer means includes a pair of rollers supporting a hammock.

3. A system according to claim 1 wherein the motion transducer is selected from the group consisting of an accelerometer, a displacement transducer and a velocity transducer.

4. A system according to claim 1 wherein the steady means further include a second rigid body having a negative impression of a portion of the ventral half of the subject's body.

5. A system according to claim 4 wherein the first and second rigid bodies are connected.

6. A system according to claim 5 wherein the first and second rigid bodies are connected by a piano hinge.

7. A system according to claim 1 further including means for minimizing the effects of movements, external to the subject, from affecting the motion transducer.

8. A ballistocardiograph system for accurately and reproducibly preparing a ballistocardiograph of a subject, the system comprising:
steady means for stationing, and thereby reproducibly positioning, a body of the subject by closefitting confinement and constraint of a large area of skin of the body;
wherein the steady means includes a first rigid body having a negative impression of a portion of the dorsal half of the body of the subject;
motion limiting means for limiting movement of the steady means to a particular linear direction of movement;
a motion transducer connected to the steady means for producing a ballistocardiograph of body motion caused by blood output through the heart by sensing motion of the steady means within which the body is stationed;
transfer means for transferring the body into and out of contact with the steady means; and
means for minimizing the effects of movements, external to the subject, from affecting the motion transducer;
wherein the means for minimizing comprises a second motion transducer coupled to the motion limiting means.

9. A ballistocardiograph system comprising:
steady means for stationing, and thereby reproducibly positioning, a body of a subject by confining and constraining a large area of skin of the body;
motion limiting means for limiting movement of the steady means to a particular linear direction of movement; and sensor means connected to the steady means for taking ballistocardiogram data from the body,
wherein the steady means includes a pair of separate rigid bodies, each having a negative impression of a portion of the subject's body.

10. A system according to claim 9 wherein one of the rigid bodies includes an impression of at least a portion of the ventral half of the subject and the other rigid body includes an impression at least a portion of the dorsal half of the subject, said dorsal half rigid body having an impresion of the portion of the subject directly below the portion of the subject impressed in the ventral half rigid body.

11. A system according to claim 10 wherein the pair of separate bodies are connected by a hinge.

12. In a ballistocardiograph apparatus having a frame; a table, elastically moveable relative to the frame, which receives a subject's body; and a means for detecting heart-beat-induced motion of the table relative to the frame; an improvement comprising:
the table includes a negative impression mold of the subject's body which when in use constrains the body sufficiently tightly so that heart-beat-induced motion and motion resonances between the mass of the subject's body and the table are reduced, a portion of the subject's skin being tightly coupled to the table, which table is coupled to the means for detecting motion.

13. The ballistocardiograph apparatus according to claim 12 wherein the table is constrained to move in a particular linear direction relative to the frame, and wherein the means for detecting motion are detecting heart-beat-induced motion of the body constrained by the mold along the particular linear direction.

14. The ballistocardiograph apparatus according to claim 13 wherein the particular linear direction is along the long axis of the body held prostrate upon the mold.

15. The ballistocaardiograph apparatus according to claim 12 wherein the mold is of a negative impression of a supine subject's body.

16. The ballistocardiograph apparatus according to claim 12 wherein the mold for constraining the subject's body is of the dorsal half of the body.

17. The ballistocardiograph apparatus according to claim 12 wherein the mold for constraining the subject's body is of oppositely disposed portions of both the dorsal and ventral halves of the subject's body.

18. The ballistocardiograph apparatus according to claim 12 further comprising:
transfer means affixed to the frame for moving the subject's body in and out of being constrained by the negative impression mold of the table.

19. In a method of taking a ballistocardiogram by fixing a subject recumbent upon a moveable platform; using the force of the subject's heart beat to move the moveable platform; and
sensing the movement of the moveable platform responsive to the subject's heart beat;
wherein the subject's heart is resiliently and compliantly coupled to the subject's great arteries which are resiliently and compliantly coupled to the subject's internal body which is resiliently and compliantly coupled to the subject's body skin and subdermal tissue, the improvement comprising:
coupling a substantial portion of the subject's skin to the moveable platform upon which the subject is recumbent;
wherein the coupling of the subject's skin is obtained by contacting with the moveable platform substantially more of the subject's skin than would be contacted by any planar surface with a headhold and with footholds and with handholds upon which the subject would, for purposes of referencing the amount of skin contacted, be recumbent.

20. The method improvement according to claim 19 wherein the subject's skin is inelastically coupled to the moveable platform.

21. The method improvement according to claim 19 wherein the coupling is by a negative impression of a portion of the body of the subject, which impression is affixed to the moveable platform, which impression receives the body portion of the subject.

22. The method according to claim 21 wherein the impression is of substantially the dorsal half of the body of the subject.

23. The method according to claim 21 wherein the impression is of substantially the ventral half of the body of the subject.

24. A ballistocardiograph system for use upon a floor comprising:
a rigid mold of a portion of the dorsal half of a subject's body;
first motion limiting means, resting on the floor, for supporting the mold above the floor, for allowing movement of the mold relative to the floor, and for limiting movement of the mold to a particular linear direction of movement, the mold being connected to the first motion limiting means;
a first motion transducer means, attached to the mold, for producing data over time responsively to the movement over time of the mold in the particular direction relative to the floor;
a reference member, separate from the rigid mold, providing a reference mass;
second motion limiting means for supporting the reference member above the floor, for allowing movement of the reference member relative to the floor, and for limiting movement of the reference member to the particular linear direction, the reference member being connected to the second motion limiting means substantially identical to the connection employed in the case of the first motion limiting means and the mold; and
a second motion transducer means, attached to the reference member, for providing data over time responsively to the movement over time of the reference member in the particular direction relative to the floor;
wherein the first motion limiting means and the second motion limiting means are coupled.

25. A ballistocardiograph system according to claim 24 further including means for comparing the time-based data taken by the first and second motion transducers.

* * * * *